United States Patent
Geller et al.

(10) Patent No.: US 9,763,614 B2
(45) Date of Patent: Sep. 19, 2017

(54) WEARABLE DEVICE AND SYSTEM FOR MONITORING PHYSICAL BEHAVIOR OF A VEHICLE OPERATOR

(71) Applicant: MAVEN MACHINES, INC., Pittsburgh, PA (US)

(72) Inventors: Avishai Geller, Pittsburgh, PA (US); Samuel J. Swerdlow, Pittsburgh, PA (US); Marc V. Gorenstein, Natlick, MA (US)

(73) Assignee: Maven Machines, Inc., Pittsburgh, PA (US)

( * ) Notice: Subject to any disclaimer, the term of this patent is extended or adjusted under 35 U.S.C. 154(b) by 0 days.

(21) Appl. No.: 14/932,709

(22) Filed: Nov. 4, 2015

(65) Prior Publication Data
US 2016/0128619 A1    May 12, 2016

Related U.S. Application Data

(60) Provisional application No. 62/076,046, filed on Nov. 6, 2014.

(51) Int. Cl.
*A61B 5/18*    (2006.01)
*A61B 5/00*    (2006.01)
(Continued)

(52) U.S. Cl.
CPC ............... *A61B 5/18* (2013.01); *A61B 5/11* (2013.01); *A61B 5/6803* (2013.01);
(Continued)

(58) Field of Classification Search
CPC ...... G08B 21/02; G08B 21/06; G08B 21/088; A61B 5/11; A61B 5/18; A61B 5/4809; A61B 5/68036; A61B 2503/22
See application file for complete search history.

(56) References Cited

U.S. PATENT DOCUMENTS

| 5,335,657 A | 8/1994 | Terry, Jr. et al. |
| 5,689,241 A | 11/1997 | Clarke, Sr. et al. |

(Continued)

FOREIGN PATENT DOCUMENTS

| EP | 2246831 A1 | 11/2010 |
| EP | 2314207 A1 | 4/2011 |
| WO | WO-2013096908 A1 | 6/2013 |

OTHER PUBLICATIONS

Hartley et al., "Review of Fatigue Detection and Prediction Technologies" National Road Commission, Sep. 2000, Melbourne, VIC.
(Continued)

*Primary Examiner* — Rene Towa
(74) *Attorney, Agent, or Firm* — Fox Rothschild LLP

(57) ABSTRACT

A system uses a wearable electronic device to monitoring behavior of an operator of a vehicle. The wearable device is worn on the head of the operator of the vehicle and includes one or more motion sensors. A processor of the wearable device or of a proximate portable electronic device receives data from the one or more motion sensors and detects a pattern of motion based on the data. The system then may determine a physiological state or physical behavior of the driver based on the detected patterns or motion. Detected physiological states may include head bobs associated with sleepiness. Detected physical behaviors may include dangerous behaviors such as phone usage, prolonged gazes, sudden lane changes, or hard braking or steering.

12 Claims, 9 Drawing Sheets

(51) Int. Cl.
    *A61B 5/11*     (2006.01)
    *B60R 1/04*     (2006.01)
    *G08B 21/24*     (2006.01)
    *G08B 21/06*     (2006.01)

(52) U.S. Cl.
    CPC ............ *A61B 5/7282* (2013.01); *A61B 5/746* (2013.01); *B60R 1/04* (2013.01); *G08B 21/06* (2013.01); *G08B 21/24* (2013.01)

(56) References Cited

U.S. PATENT DOCUMENTS

| | | | |
|---|---|---|---|
| 5,841,354 | A | 11/1998 | Bae et al. |
| 6,920,229 | B2 | 7/2005 | Boesen |
| 6,946,965 | B2 | 9/2005 | Young et al. |
| 7,209,569 | B2 | 4/2007 | Boesen |
| 2008/0174451 | A1 | 7/2008 | Harrington et al. |
| 2011/0001623 | A1 | 1/2011 | Kim |
| 2012/0218410 | A1 | 8/2012 | Kim et al. |
| 2014/0072136 | A1* | 3/2014 | Tenenbaum et al. ........... 381/74 |
| 2014/0121897 | A1 | 5/2014 | Felkins et al. |
| 2014/0168399 | A1 | 6/2014 | Plummer et al. |
| 2014/0172467 | A1* | 6/2014 | He et al. ........................ 705/4 |
| 2014/0191858 | A1* | 7/2014 | Morgan ............... G07C 5/0816 340/439 |
| 2015/0161894 | A1* | 6/2015 | Duncan et al. ................. 705/4 |

OTHER PUBLICATIONS

Haworth et al., "Testing of Commercially Available Fatigue Monitors" Monash University Accident Research Centre, May 1991, Report No. 15.

May et al., "Driver fatigue: The importance of identifying causal factors of fatigue when considering detection and countermeasure technologies" Transportation Research Part F, 2009, vol. 12, pp. 218-224.

* cited by examiner

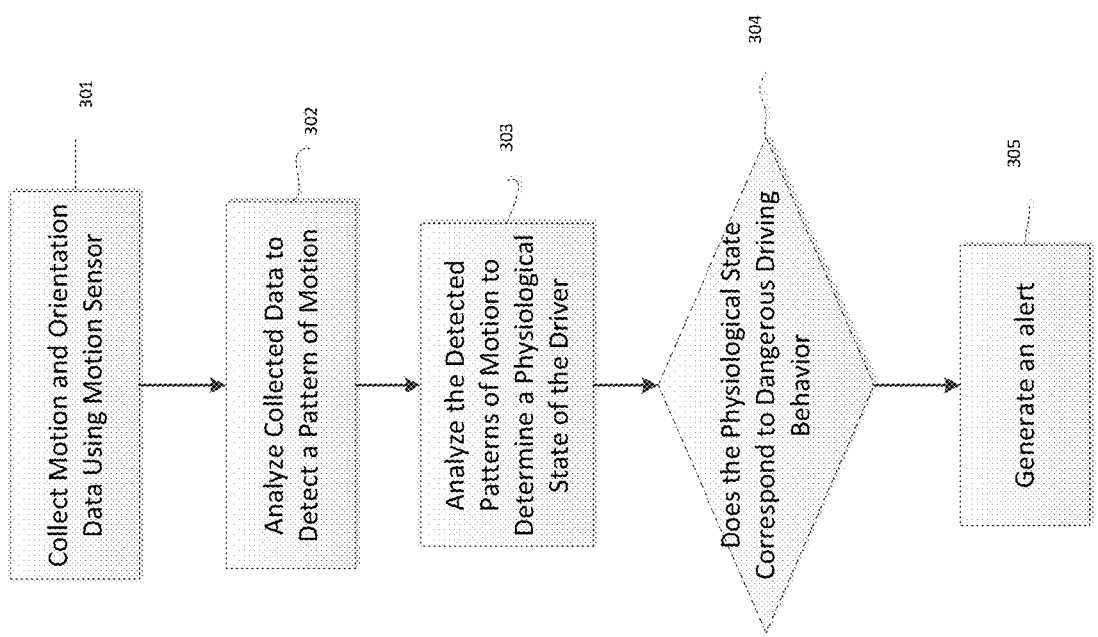

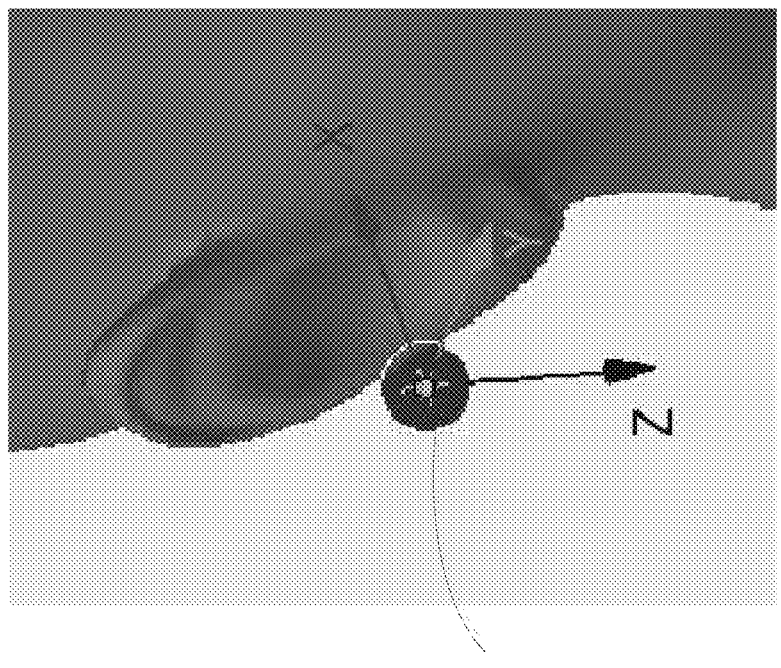

WEARABLE DEVICE AND SYSTEM FOR MONITORING PHYSICAL BEHAVIOR OF A VEHICLE OPERATOR

RELATED APPLICATIONS AND CLAIM OF PRIORITY

This patent document claims priority to U.S. provisional patent application No. 62/076,046, filed Nov. 6, 2014, the disclosure of which is hereby incorporated by reference in full.

BACKGROUND

Professional drivers such as truck drivers and bus drivers are responsible for operating large, heavy, and dangerous vehicles carrying valuable cargo and human lives. Additionally, they spend many hours and days driving and are susceptible to fatigue and distraction (outside or inside the vehicle) at any time. It only takes a few seconds of a lapse of attention to cause a tragic accident resulting in a loss of life. As a result, each year numerous automotive accidents and fatalities occur because of sleepy or fatigued individuals falling asleep while driving, or distracted individuals failing to respond to changing road or traffic conditions.

It has been observed that these drivers exhibit certain physiological patterns (or driver behaviors) that are predictable and detectable. Examples of such physiological patterns or driver behaviors include head-bobs, frequency of mirror checks (the Federal Motor Carrier Safety Administration, FMCSA, suggests that an alert driver should check mirrors every 5 to 8 seconds), looking at gauges, continuous forward gaze, hard braking, corrective steering behaviors (such as hard steering), looking down for extended periods of time, looking out the side windows for extended periods of time, failure to wear the seatbelt, sudden lane changes and/or drifting, and other similar patterns or behavior.

Systems which detect and warn of driver impairment are known, but many are limited in their effectiveness, in that they cannot reliably and consistently detect driver impairment, and thus may give false warnings when the driver is unimpaired, or worse, fail to give warnings when the driver is impaired. Furthermore, existing solutions merely check for certain driver physiological states such as fatigue based on one or two of the above driver behaviors or patterns. However, there is a need for estimating other driver physiological states such as alert driver, focused driver, distracted driver, drowsy driver, fatigued driver, etc. based on a comprehensive analysis of more types of driver behaviors, in order to not only reduce accidents, but also to promote compliance with laws and general good driving.

This document describes a new device, system and method that can monitor various physiological patterns or driver behaviors of a driver, calculates a physiological state of the driver, and provide suitable alerts to prevent accidents.

SUMMARY

In one aspect of the disclosure, a system (and method) for monitoring behavior of an operator of a vehicle may include a wearable electronic device configured to be worn on the head of an operator of the vehicle, wherein the wearable electronic device may include a motion sensor, a processor, and a computer-readable medium containing programming instructions. In an embodiment, the programming instructions, when executed, will cause the processor to receive a set of data from the motion sensor and analyze the set of data to detect a pattern of motion. The system may then access a data set corresponding to a plurality of patterns of motion, and use the data set to analyze the detected pattern of motion to determine a physiological state of the operator of the vehicle based on the detected pattern of motion. Detected physiological states may include, for example, head bobs associated with sleepiness. Detected physical behaviors may include, for example, dangerous behaviors such as phone usage, prolonged gazes, sudden lane changes, or hard braking or steering.

In an embodiment, the system may determine that the physiological state comprises drowsiness if the detected pattern of motion is a head bobbing motion by analyzing the set of data from the motion sensor to determine jerk and jounce associated with movement of the head of the operator. The system may then determine, based on the jerk, that the head dropped forward and then pulled back upward, and determine, based on the jounce, that a rate of change of acceleration occurred while the head dropped forward and then pulled back upward such that the determined rate of change of acceleration corresponds to a head bob.

In at least one embodiment, the system may also include a portable electronic device having a receiver, and the wearable electronic device may further include a transmitter configured to transmit the set of data to the receiver of the portable electronic device. In an embodiment, the processor and the computer-readable medium may be included within the portable electronic device. Alternatively and/or additionally, the system may include a data storage facility, and a computer-readable medium containing programming instructions that, when executed, will instruct the processor to: store the determined physiological state in the data storage facility as part of a profile for the vehicle operator, analyze the physiological state with previously-stored physiological states for the vehicle operator to generate a score for the vehicle operator, and output the score.

In an embodiment, using the data set to analyze the detected pattern of motion and determine a physiological state of the operator of the vehicle based on the detected pattern of motion may include determining whether the detected pattern of motion corresponds to a prolonged forward gaze, a prolonged side gaze, a swaying motion, or a head bob and is repeated during a time period; if so, determine that the physiological state of the operator is fatigued.

In some embodiments, the system may also determine a plurality of physiological states of the operator of the vehicle during a time period, assign a score to each of the plurality of physiological states of the operator of the vehicle, calculate an overall score for the operator of the vehicle, and use the overall score to determine a quality of the operator of the vehicle.

In another aspect of the disclosure, a system (and method) for monitoring behavior of an operator of a vehicle is disclosed. The system may include a wearable electronic device configured to be worn on the head of an operator of the vehicle, a processor, and a computer-readable medium containing programming instructions. The programming instructions may instruct the processor to receive a first set of data from a motion sensor of the wearable electronic device, analyze the first set of data to detect a pattern of motion, access a data set corresponding to a plurality of patterns of motion, use the data set to analyze the detected pattern of motion and determine a physical behavior of the operator of the vehicle based on the detected pattern of motion, and generate an alert if the determined physical behavior corresponds to a dangerous operator behavior.

In an embodiment, determined physical behavior corresponds to a dangerous operator behavior if the detected pattern of motion corresponds to a prolonged forward gaze, a prolonged size gaze, a phone usage event, a hard braking event, a sudden lane change, or a hard steering event.

In one embodiment, the system may analyze the first set of data to detect a pattern of motion by detecting a head rotational motion of the operator of the vehicle by: determining a forward-facing direction position as a position corresponding to the most common orientation of the wearable device; determining, based on the first set of data from the motion sensor, angular displacement of the operator's head; and determining whether the angular displacement corresponds to a side gaze, or a forward gaze. Additionally and/or alternatively, the may determine the physical behavior by determining whether the operator exhibited a forward gaze or a side gaze for an extended period of time.

In one embodiment, the system may analyze the first set of data to detect a pattern of motion by detecting a head rotational motion of the operator of the vehicle by: determining a forward-facing direction position as a position corresponding to the most common orientation of the wearable device, determining, based on the first set of data from the motion sensor, angular displacement of the operator's head determining, based on the first set of data from the motion sensor, angular displacement of the operator's head, and determining whether the angular displacement corresponds to a phone usage event, wherein the phone usage event remained constant for at least a threshold period of time. Additionally and/or alternatively, the may determine the physical behavior by determining that the operator exhibited dangerous operator behavior if the system detected a phone usage event for at least a threshold period of time.

In at least one embodiment, the system may also include a reference device that is attached to the vehicle. The reference device may include a transmitter, and a reference device motion sensor that is configured to collect a second set of data corresponding to motion of the vehicle. In some embodiments, the system may receive the second set of data from the transmitter. The system may then determine that the physical behavior corresponds to a hard braking event if: the first set of data indicates that the motion sensor of the wearable electronic device is experiencing a negative acceleration above a threshold value, at the same time, the second set of data also indicates that the motion sensor of the reference device is experiencing a negative acceleration above a threshold value. Additionally and/or alternatively, the system may determine that the physical behavior corresponds to a sudden lane change event if: the first set of data indicates that the motion sensor of the wearable electronic device is experiencing a rate of change in a z-plane exceeding a threshold value within a threshold time, at the same time, the second set of data also indicates that the motion sensor of the reference device is experiencing is experiencing a rate of change in the z-plane exceeding the threshold value within the threshold time. Additionally and/or alternatively, the system may analyze a derivative of the first set of data and the second set of data, and determine that the physical behavior corresponds to a hard steering event if the derivative has a value that exceeds a threshold.

In some embodiments, the wearable electronic device may also include a housing, and the first processor and the computer-readable medium are included within the housing.

In yet another embodiment, the system may further include a portable electronic device having a receiver, and the wearable electronic device may include a transmitter configured to transmit the first set of data to the receiver of the portable electronic device. In an embodiment, the processor and the computer-readable medium may be included within the portable electronic device.

BRIEF DESCRIPTION OF THE DRAWINGS

FIG. 3 is a flowchart method for detecting physiological patterns and a physiological state for a driver, according to an embodiment.

FIGS. 4A, 4B, and 4C illustrate example frame of reference systems for a wearable electronic device, a portable electronic device, and the world, according to an embodiment.

DETAILED DESCRIPTION

As used in this document, the singular forms "a," "an," and "the" include plural references unless the context clearly dictates otherwise. Unless defined otherwise, all technical and scientific terms used in this document have the same meanings as commonly understood by one of ordinary skill in the art. As used in this document, the term "comprising" means "including, but not limited to."

In this document, an "electronic device" refers to a device that includes a processor and one or more hardware components such as a non-transitory, computer-readable memory. The memory may contain programming instructions that, when executed by the processor, cause the electronic device to perform one or more operations according to the programming instructions. Examples of electronic devices include personal computers, servers, mainframes, gaming systems, televisions, and portable electronic devices such as smart phones, personal digital assistants, tablet computers, laptop computers, cameras, media players and the like.

"Electronic communication" refers to the ability to transmit data via one or more signals between two or more electronic devices, whether through a wired or wireless network, and whether directly or indirectly via one or more intermediary devices.

When this document uses the term "processor" or "processing device," unless expressly stated otherwise it is intended to include embodiments that consist of a single data processing device, as well as embodiments that include two or more data processing devices that together perform various steps of a described process.

When this document uses the terms "memory," "memory device," "computer-readable memory," "computer-readable medium," or "data storage facility," unless expressly stated otherwise it is intended to include embodiments that consist of a single memory device, embodiments that include two or more memory that together store a set of data or instructions, or a sector or other portion of a memory device.

Figure 1:
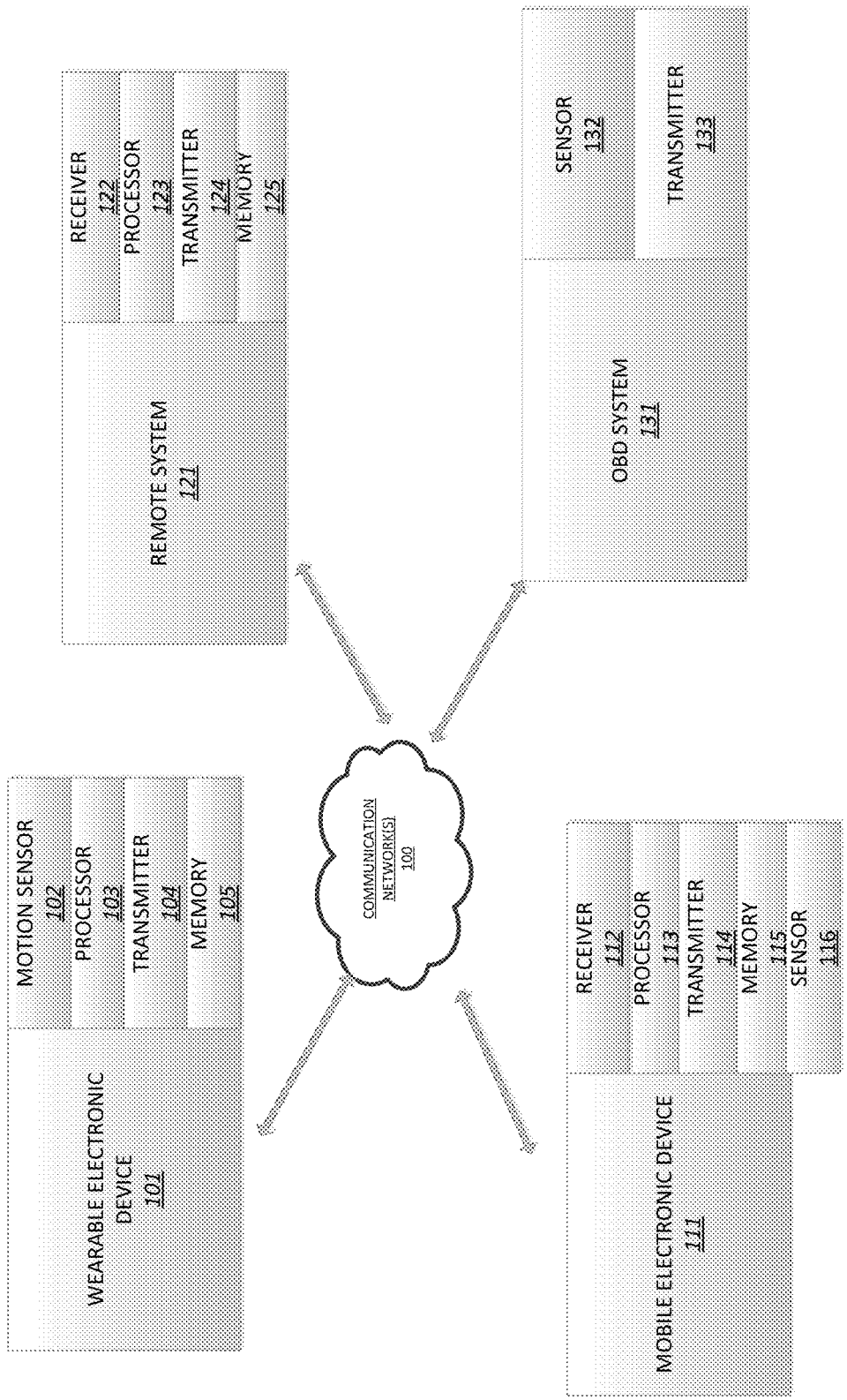
FIG. 1 is a block diagram that illustrates various elements that may be included in a driver monitoring system, according to an embodiment.

FIG. 1 is a block diagram that illustrates various elements of a system for monitoring behavior and physiological states of an operator of a vehicle, such as a car driver, truck driver, bus driver, train conductor, airline pilot, or the like. Various devices in the system may communicate with each other via one or more communication protocols and/or networks 100. Examples may include, without limitation, WiFi, short-range communications such as Bluetooth, cellular networks, Zigbee, and other similar networks and/or protocols.

The system includes a wearable electronic device 101 configured to be worn on the head of a vehicle operator. The wearable electronic device 101 may include a motion sensor 102 such as an accelerometer and/or gyroscope that generates an electronic signal that is indicative of one or more directions of movement, speeds of movement, acceleration, and/or orientation of the device. In an embodiment, the wearable electronic device 101 may also include a location determining device (e.g., a GPS signal receiving device), and the processor may use signals from the GPS signal receiving device to perform location based operations. In certain other embodiments, the wearable electronic device 101 may also include other sensors such as heart rate sensors, an imaging device (i.e., a video or still image camera), a barometer, and a temperature sensor.

The wearable device may also include a processor 103 that is in electronic communication with the motion sensor so that it can receive data generated from the motion sensor and generate data for delivery to another device. The generated data may be the received data, or it may be processed data that results from the processor performing one or more operations on the received data as described below. The wearable device 101 may also a wireless transmitter 104 that is capable of transmitting data that the first processor outputs via a wireless communication protocol such as Bluetooth, Bluetooth Low Energy (BLE), radio frequency identification (RFID), Zigbee, near-field communication (NFC), Wi-Fi, 4G/LTE, or one or more other near-field or short-range communication protocols. The processor may also be in communication with a clock module and receive time data generated by the clock module for use in various methods described below. In an embodiment, the wearable electronic device may also include a speaker and/or a microphone to transmit audio messages to and/or receive audio messages from a user of the wearable electronic device. In an embodiment, the wearable electronic device may also include a feedback mechanism (such as a vibrator) to transmit feedback messages to a user of the wearable electronic device.

Figure 2:
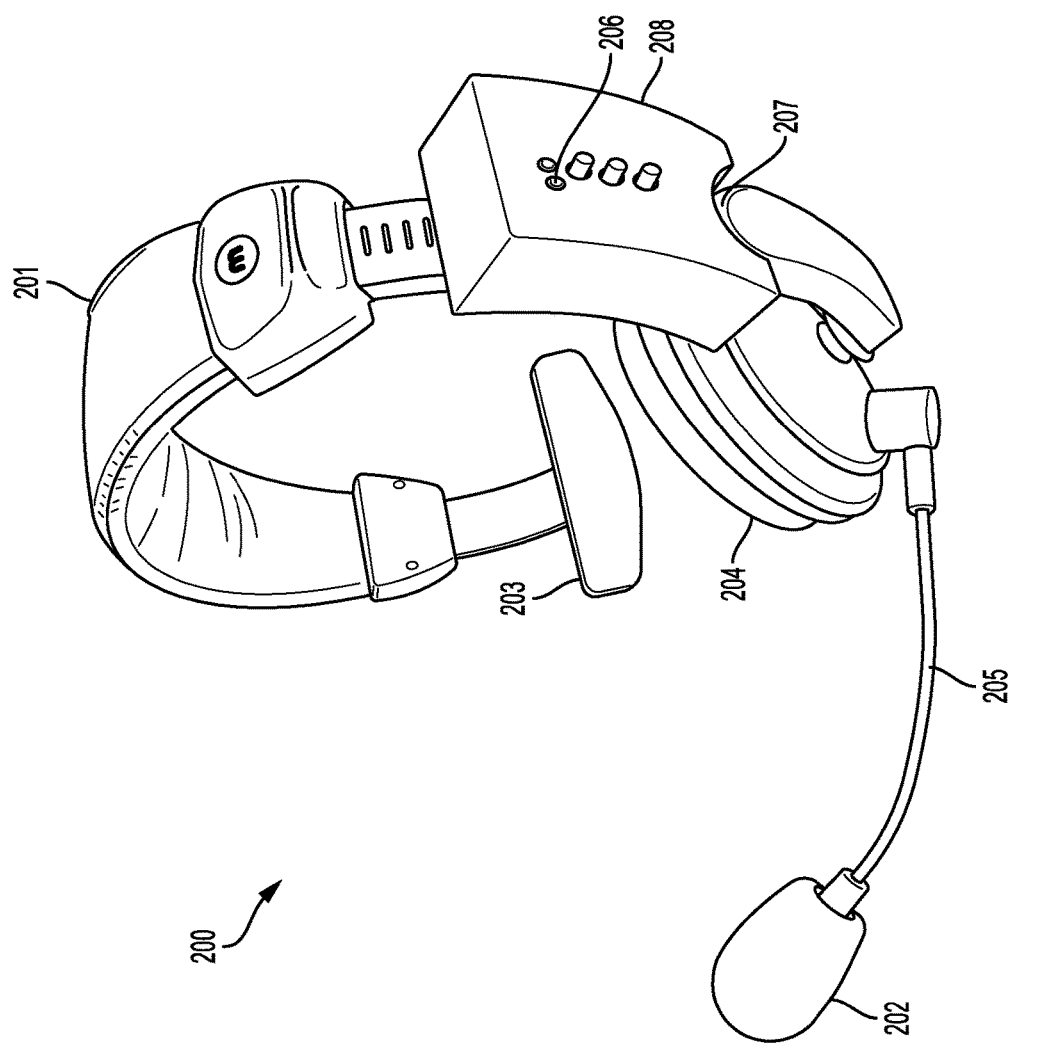
FIG. 2 is an example embodiment of a wearable electronic device.

Examples of suitable wearable electronic devices 101 include headset devices such as headphones, over-ear devices, in-ear devices, and the like. For example, as shown in FIG. 2, the wearable electronic device 200 may be a headset that includes a microphone 202 and speaker 204 that enables the wearer to transmit and receive audio communications to and from a smartphone or other portable electronic device via a near-field or short-range communications protocol. The microphone 202 may be attached to the device 200 via a rigid or a flexible arm 205 configured to transmit the received audio signals to a processor of the wearable electronic device 200. The wearable electronic device 200 may be configured to be mounted over the head of a user via an anchor 203 and a flexible headband 201. The flexible headband 201 may be adjustable to account for different head sizes of users. The wearable electronic device 200 may also include a housing 208 that may include various components such as the processor, the motion sensor, the GPS receiving device, the transmitter components 206, etc. The wearable electronic device 200 may further include a power source and/or a charging port 207.

Returning to FIG. 1, the system may also include a portable electronic device 111 that includes a receiver 112 such as an antenna that is configured to receive the data transmitted from the transmitter 104 of the wearable electronic device 101. The configuration will be such that the receiver 112 can receive data transmitted by the transmitter's 104 wireless communication protocol. The portable device 111 will also include a processor 113 and may include a transmitter 114 that can transmit data generated by the processor 113 or relay data received by the receiver 112. The transmitter 114 and receiver 112 may be separate devices, or they may be components of a single device such as a transceiver. The portable electronic device 111 may include one or more sensors 116 such as a motion sensor, a GPS signal receiving device, heart rate sensors, an imaging device (video or still image, i.e., a camera), etc. In an embodiment, the portable electronic device may also include a speaker and/or a microphone to transmit to and/or receive from a driver of the vehicle, audio messages. In an embodiment, the portable electronic device may also include a feedback mechanism (such as a vibrator) to transmit feedback messages to a user of the wearable electronic device.

Examples of suitable portable electronic devices 111 include smartphones, laptop computing devices, tablet computing devices, global positioning systems, electronic devices that are integrated into the vehicle such as dashboard consoles, and the like. Examples of such devices will be discussed below in the discussion of FIG. 6.

The system also includes a computer-readable medium containing programming instructions that, when executed, cause the portable device processor 113, the wearable device processor 103, both processors and/or other processing devices to: (i) analyze data received from the motion sensor and/or a processor to detect a pattern of motion of the wearer of the wearable device; (ii) analyze the detected pattern of motion to determine the physiological state of the drive, (iii) determine whether the pattern of motion and/or the physiological state corresponds to a dangerous driver behavior; and (iii) if the pattern of motion and/or the physiological state corresponds to a dangerous driver behavior, generate an alert. The computer-readable medium may be a memory 105 of the wearable electronic device, a memory 115 of the portable electronic device, or a memory 125 of another device such as a remote system 121 that is in wireless communication with the wearable electronic device 101 and/or the portable electronic device 111.

For example, the instructions may cause the processor to analyze sensed motion data and determine whether the motion is indicative of the vehicle operator exhibiting a dangerous behavior such as drowsiness, fatigue, distraction, or sleep. For example, the system may use data from sensors contained in the device 101 worn on the driver's head to detect motion and/or physiological signs indicative of drowsiness, fatigue, distraction, or sleep.

The system may also include an on-board diagnostics system (OBD) 131 of the vehicle that serves as a reference device and which is in communication with the wearable electronic device 101, the portable electronic device 111, and/or the remote system 121, via a transmitter 133. The OBD system 131 may also include one or more sensors 132 that are able to sense corresponding to the vehicle operation and motion. As with the wearable and portable electronic devices, the sensors of the OBD system may include motion sensors such as accelerometers and/or gyroscopes, or they may be sensors that are receive data from other vehicle equipment (such as the speedometer) to determine motion-related data. In an embodiment, the OBD system may collect data relating to the operation of the vehicle and transmit it to the various other devices of the system. In an embodiment, the OBD system may also include a speaker and/or a microphone to transmit audio messages to and/or receive audio messages from a driver of the vehicle.

FIG. 3 illustrates a flowchart corresponding to the method for analyzing the data received from the motion sensor and/or one or more processors to detect a pattern of motion and a physiological state of the driver, according to an embodiment.

Figure 4B:
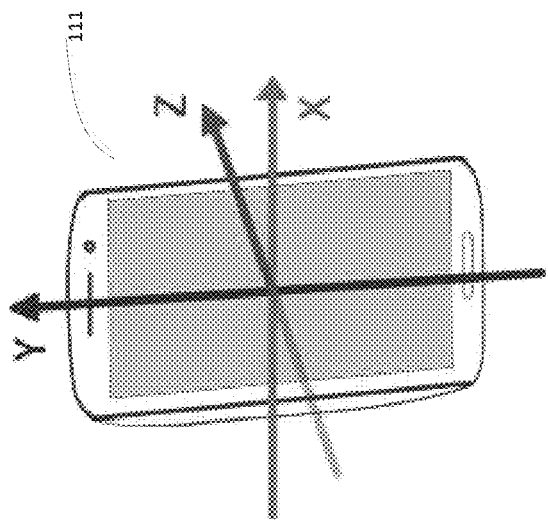
Figure 4C:
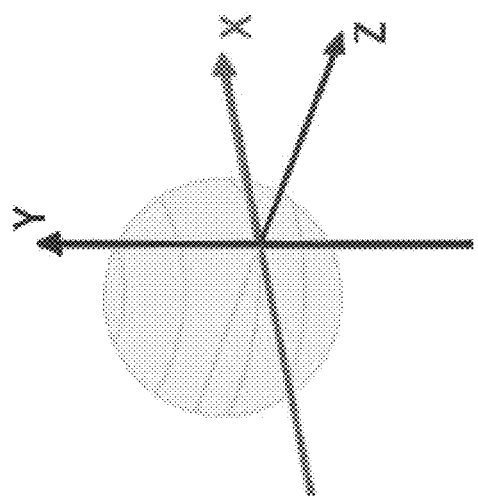

In step 301, the wearable electronic device may collect motion and orientation data using its motion sensors. The motion and orientation data may include, without limitation, one or more directions of movement, speeds of movement, acceleration, and/or orientation of the device. In an embodiment, the data may indicate the current position, motion and/or orientation of the wearable electronic device. In some embodiments, the position, motion and/or orientation may be collected as an absolute position and orientation, such as the geographical coordinates of the wearable electronic device and the cardinal direction (north, south, east, west) of the wearable electronic device relative to the Earth. Alternatively and/or additionally, the position, motion and/or orientation may be collected or processed to obtain data relative to a local point of reference (in an x, y, z and/or other frame of reference), such as a neutral position and orientation of a user's head (discussed below). Example frames of references for the wearable electronic device, the portable electronic device, and the Earth are illustrated in FIGS. 4A, 4B, and 4C, respectively. FIG. 4A illustrates the x, y, and z directions for a wearable electronic device 101 worn over the ear of a driver looking forward in a vehicle driver seat, according to an embodiment.

In an embodiment, the data may indicate a change in position, motion, and/or orientation of the wearable electronic device, such as the change in position and orientation within a time interval. Alternatively and/or additionally, the data may indicate a combination of these types of information, or indicate other types of information. In an embodiment, the position and/or orientation data of the wearable electronic device may include data such as yaw, pitch and roll of the wearable electronic device, and may be indicative of the position and/or orientation of the head of the wearer (i.e., the driver). In an embodiment, the motion data of the wearable electronic device may include distance travelled by the wearable electronic device in a linear or a rotational direction, linear and/or angular velocity of the movement, linear and/or angular acceleration of the movement, and/or associated time interval(s). The data may be collected and analyzed continuously and/or at fixed intervals of time for detecting one or more patterns of motion.

While the current disclosure collects and analyzes data from motion sensors to detect patterns of motion and determine the physiological state of the vehicle operator, data from other sensors such as a camera, barometer, and temperature sensor may also be used for the same. For example, the system may use a rule set that defines a threshold temperature, air pressure and/or humidity value (inside the vehicle) above which there may be a higher likelihood of the vehicle operator being fatigued and/or drowsy. In an embodiment, the system may compare the collected temperature and/or humidity values from the temperature sensor with the threshold values and use the comparison with the data collected from the motion sensors. For example, the system may adjust the threshold values, time intervals, etc. in the analysis of motion sensors' data (as discussed below) based on this comparison. In yet another embodiment, the system may use real-time images collected from the camera to determine the motion and/or position of the vehicle operator's head and/or eyes.

In step 302, a processor of the wearable electronic device (and/or the portable electronic device) may analyze the collected data to detect one or more patterns of motion, which may correspond to or driver actions by, or physiological state of, the vehicle operator. In an embodiment, the acquired data may be analyzed using digital signal processing algorithms (discussed below) to compute, analyze, and determine motion in time and frequency domains. As discussed above, examples of patterns of motion may include, without limitation, patterns of motion that correspond to the driver experiencing a head bobs, performing mirror checks, looking at gauges, having a continuous forward gaze, hard braking (i.e., suddenly and severely applying the brakes of the vehicle), corrective steering behaviors (such as hard steering), looking down for extended periods of time (which may correspond to mobile phone usage), looking out the side windows for extended periods of time, failure to wear the seatbelt, sudden lane changes and/or drifting, and other similar patterns or behavior.

In an embodiment, the processor may analyze the collected motion sensor data to detect a head bob pattern of motion. The classic "head bobbing" motion, where the driver's head drops and then quickly pulls back upward is one of the patterns that is often exhibited when an individual is becoming drowsy while seated in an upright position. In an embodiment, the head bob pattern of motion may be detected by analyzing the collected motion sensor data to determine the jerk and jounce of a movement of the wearer's head, and analyzing the jounce. Jerk is defined as the third derivative of a position vector with respect to time (first derivative of acceleration). Jounce is defined as the fourth derivative of a position vector with respect to time (second derivative of acceleration). In a head bob, the driver's head drops and suddenly pulls back. This may be detected by measuring the jerk and determining whether the value of the jerk is of a magnitude that corresponds to a known head bob value. If so, the system may analyze the rate of change of acceleration (using jounce) associated with the directional change between the head drop and the pull back. If the value of the rate of change is also of a magnitude that corresponds to a known head bob value, then the system will determine that a head bob occurred and that the driver is likely exhibiting drowsiness.

Figure 5A:
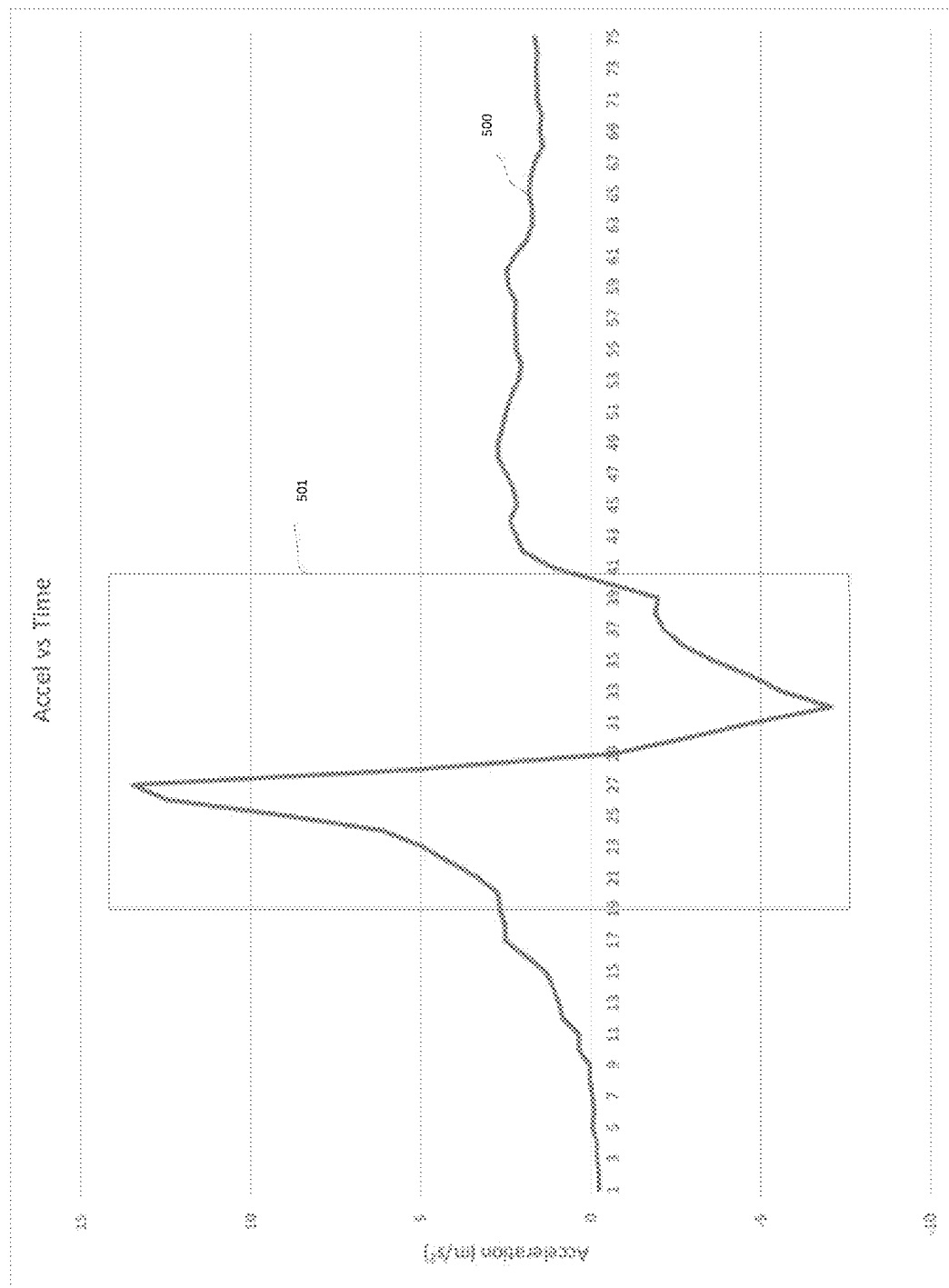
FIG. 5A and FIG. 5B are graphical illustrations for calculation of jerk and jounce for detecting a head-bob type patterns of motion, according to an embodiment.

For example, using the frame of reference of the wearable electronic device (FIG. 4A), data corresponding to linear acceleration in the y-direction (calculated using data collected from an accelerometer), and the rotation along the x-direction (calculated using data collected from a gyroscope) may be analyzed. In an embodiment, for analysis, the head movement data may be collected at a constant sample rate of at least 20 times/second. Other sampling rates such as 30 times/second, 15 times/second, 25 times/second, etc. are within the scope of this disclosure. FIG. 5A shows the raw measurement acceleration data 500 of corresponding to the head movement of a driver, with respect to time. Section 501 of the graph in 5B illustrates the change in acceleration of the head for a single head bob movement. In a classic head bob pattern of motion, the acceleration increases while the head is going down and is maximum just before the bottom most point of the head bob, becomes zero at the bottom most point, then changes direction and increases in the backward pull motion again till it reaches a maximum, and then becomes zero again. In another embodiment, an auto-correlation function may be used for the above analysis.

Figure 5B:
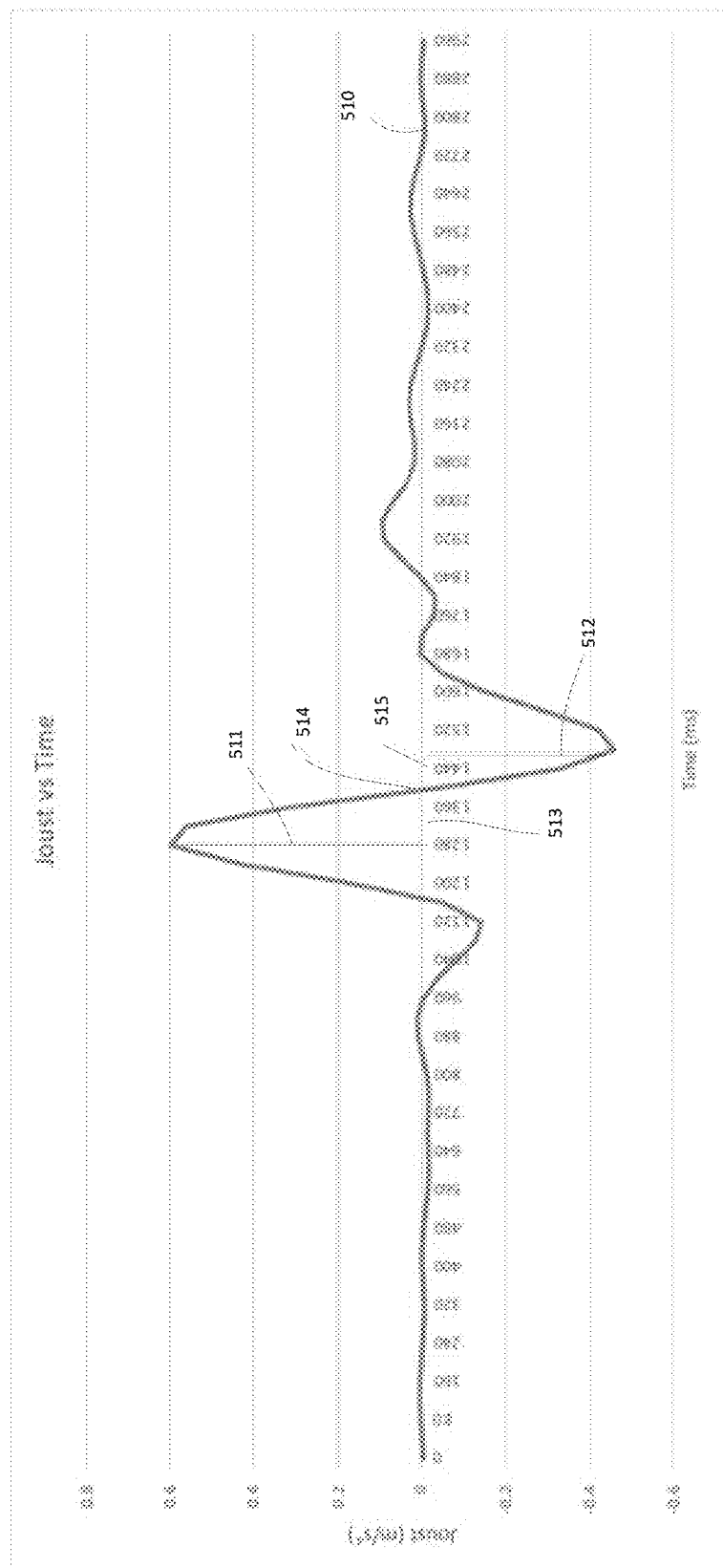

The sampled data is processed to determine a second derivative of the acceleration, with respect to time, to retrieve a jounce signal 510 of the acceleration signal (FIG. 5B). The second derivative may be determined by passing a signal indicative of the collected acceleration data through a second derivative filter (not shown here), in accordance with methods now or hereafter known to those skilled in the art. In an embodiment, the signal may be passed through a smoothing filter before determining the second derivative, to reduce noise and other fluctuations.

The jounce may then be analyzed to detect a head bob if the jounce signal changes signs from positive to negative, or vice versa. In an embodiment, two consecutive peaks may be analyzed simultaneously, and the amplitudes and duration of the peaks may be compared to threshold values indicative of a head bob motion to detect whether or not the jounce signal represents a head bob motion. For example, in an embodiment, the threshold values indicative of a head bob motion are as follows: the amplitude of the first peak (511) must be at least about 0.01875 m/s$^4$, the amplitude of the second peak (512) must be at least about 0.0125 m/s$^4$, the amount of time (513) from the first peak's maximum to the shared zero crossing 515 (between the two peaks) must be less than or equal to about 200 ms, and the amount of time from the shared zero crossing to the second peak's maximum (514) must be less than or equal to about 200 ms. These threshold values are provided by way of example only and other, now or hereafter known, threshold values indicative of a head bob motion pattern are within the scope of this disclosure. In an embodiment, the threshold values may be calculated and/or updated by the system periodically based on truth data, as discussed below.

If the jounce signal satisfies a set of threshold values, the absolute value of the x-axis rotational data may also be integrated over a period of time (such as the past the past 2, 3, or 4 seconds) to ensure that a threshold degree of rotation has occurred. In an embodiment, the threshold degree of rotation is between about 85 to 100 degrees, such as 85 degrees, 90 degrees, and 95 degrees. The integration may be performed for other time ranges without deviating from the principles of the disclosure. The system may detect a head bob motion if the jounce signal satisfies the threshold values and at least the threshold amount of rotation has occurred.

The above method for detecting a head bob pattern of motion is provided merely as an example, and other now or hereafter known methods are within the scope of this disclosure.

In another embodiment, the processor may analyze the collected motion sensor data to detect a pattern of motion indicative of head position and/or a gaze position of the driver. Examples of head and/or gaze positions may include, without limitation, mirror checks, forward gaze, side gaze, looking at gauges, looking out the windows, and looking down. In various embodiments, a determination that a driver is looking in any direction (e.g., forward, side, down such as toward a phone, or in another direction) for a threshold continuous period of time may be considered to be a dangerous vehicle operator behavior. In addition or alternatively, a determination that detected pattern of motion corresponds to a prolonged (i.e., more than a threshold time period in duration) forward gaze, a prolonged side gaze, a swaying motion, or a head bob, and also determining that the pattern is repeated at least a certain number of times or lasts at least a certain duration during a time period, may be indicative that the driver's physiological state is fatigued.

In an embodiment, a rotational motion (using data corresponding to direction and orientation) of the driver's head along with the degree of rotation and the direction rotation may be used to detect a pattern of motion indicative of head position and/or a gaze position of the driver. Additionally and/or alternatively, time intervals corresponding to the detected rotational motion may also be analyzed. In an embodiment, the rotational motion of the driver's head may be analyzed with respect to the rotational motion of a reference device within the vehicle to account for the common mode signal, i.e., the vehicle's motion such as during a turn. Examples of reference device may include without limitation, a portable electronic device within the vehicle, the onboard diagnostics system (OBD), and/or any other device within the vehicle that includes a motion sensor. The reference device may transmit data corresponding to the rotational motion (direction and orientation) collected using the motion sensors, of the reference device itself, which may be indicative of the vehicle's motion.

In an embodiment, to detect a pattern of motion indicative of head position and/or a gaze position of the driver, rotation matrices that relate the reference frames of the wearable electronic device (FIG. 4A) and the reference device (FIG. 4B) with respect to Earth (FIG. 4C) are first generated from the wearable electronic device's and the reference device's orientation (using methods now or hereafter known to those skilled in the art). For example, in an embodiment, the forward facing direction (i.e., the y-direction in FIG. 4A) for the wearable device may be determined based on the assumption that the driver is looking forward most of the times. Hence, the direction the wearable electronic device is facing for a threshold amount of time is assumed to be the forward direction. A unit vector of the forward direction may then be multiplied into the cosine matrix (or the quaternions) to generate the forward direction in the Earths' reference frame.

Next, gyroscope readings in each direction (x, y, and z) for the wearable electronic device and the reference device may be recorded. Finally, the projection of each internal axis onto the world's Z axis may be multiplied by the corresponding axis' gyroscope reading to determine the rotation of the wearable electronic device and the reference device, in the world's reference frame. The reference device's rotational motion may then be subtracted from that of the wearable electronic device. In an embodiment, the constant bias of the gyroscopes (average output when the gyroscope is sitting still) for the wearable electronic device and the reference device may then be subtracted to eliminate bias and drift error (for example, using an edge detection filter).

The rotation motion signal may then be integrated to obtain the angular displacement of the driver's head relative to an initial position. In certain embodiments, the integral may be passed through a high-pass filter to remove the zero frequency signal. The width of the edge detection filter may be 2 seconds, 3, seconds, 4 seconds, or similar other widths.

In an embodiment, magnitude and direction of the angular displacement may be analyzed to detect a pattern of motion indicative of head position and/or a gaze position of the driver. In an embodiment, the time interval corresponding to the angular displacement (i.e., the time for which a driver's head stayed in a certain position) may also be analyzed. Various threshold values indicative of different types of patterns (such as mirror checks, forward gaze, looking outside the window, etc.) may be pre-defined. Alternatively and/or additionally, the threshold values may be calculated and/or updated periodically based on truth data (as discussed below). The truth data may be used for adjusting the threshold values based on the model and make of the vehicle, height of the driver, location of the sensors, level of fatigue/alertness of the driver, or other similar variables.

If the driver's head is in a particular period (e.g., looking forward, looking to the side, etc.) for an extended period of time (i.e., a continuous period of time that exceeds a threshold value), the system may determine that the driver may be exhibiting dangerous driver behavior.

For example, in an embodiment, if the summed angle of the angular displacement is above a first threshold such as 10 degrees, 12, degrees, 15 degrees, or 20 degrees, a left mirror check event is detected. In addition, if the summed angle of the angular displacement is below second threshold such as −20 degrees, −25 degrees, or −30 degrees, a right mirror check is detected. Distance between the mirrors and the driver (in the XY plane of the world) may be used to determine the above threshold values.

In some embodiments, the system may determine whether the driver is complying with a mirror check procedure. As noted elsewhere in this document such a procedure may require that the driver check each side and/or rear mirror every 5-8 seconds, or at some other appropriate time interval. The system also may include a clock module, and the system may use clock data from the clock module to determine whether the vehicle operator has performed a mirror check at least once during the required time interval.

In an embodiment, a mirror check event may then be distinguished from a pattern of motion corresponding to the driver simply looking outside the window, by analyzing the time interval. For example, if the time interval for which a driver is looking to the left or to the right is more than 5 seconds (in addition to the above values of summed angle), the system may detect that the driver is looking outside the window and not checking a left/right mirror. Additionally and/or alternatively, the mirror check detection may be limited to a threshold range of summed angle such as 10-25 degrees, 15-25 degrees, or 20-30 degrees for left mirror check, [−20]-[−30], [−30]-[−40] degrees, or [−35]-[−45] for right mirror checks, and a "looking outside the window" pattern may be detected if the summed angle is above threshold value for the left window or below a threshold value for the right window.

Similarly, direction and magnitude of the angular displacement may be used to detect a forward gaze (about 0-5 degree rotation for a threshold interval of time), downward gaze (maybe indicative of checking of gauges if the downward rotation is equal to a threshold value such as 15 degrees or 20 degrees), and other similar patterns.

In an embodiment, a pattern of motion corresponding to phone usage (such as texting) may be detected by analyzing the collected motion sensor data. For example, the above algorithm for analyzing the magnitude and direction of the angular displacement may be used to detect that a driver is looking downward and to the right, and the time interval may be compared to a threshold to detect that the driver is using a phone. Alternatively and/or additionally, phone usage pattern of motion may also be detected using motion sensors associated with the phone to detect movement and/or orientation change of the phone.

In another embodiment, a pattern of motion corresponding to hard braking may be detected by analyzing the acceleration along the forward direction for the reference device. Large negative accelerations (above a threshold value) in the forward direction may be indicative of hard braking. Alternatively and/or additionally, if a driver is wearing a seat belt, the jounce of the head upon hard braking may be analyzed to detect a pattern of motion indicative of hard braking. Similarly, sudden lane changes may be detected based on a rate of change of direction in the z-plane exceeding a predetermined value within a predetermined time (for the reference device and/or the vehicle OBD sensors).

In another embodiment, a pattern of motion corresponding to hard steering may be detected by analyzing the derivative of the gyroscope readings (rotational readings) of the vehicle and comparing them to a threshold value.

In yet another embodiment, a rhythmic and/or swaying pattern of motion may be detected by analyzing the rotational data of the wearable electronic device and/or the reference device. For example, in an embodiment, a large fast fourier transform (FTT) may be performed on the roll, pitch, and yaw signals and compared to a threshold. Large values at frequencies around 1 Hz may indicate swaying.

In an embodiment, the various threshold values to be used in the above pattern detection step, may be calculated and/or updated periodically based on a training model developed from ground truth data. Such adaptive threshold values may be employed to account for the variations in the vehicle (such as type, model, etc.), the driver of the vehicle (such as height of the driver, driving skills, etc.), and other conditions such as time of the day, traffic conditions, current trip driving time, and other similar variables. "Ground truth" refers to the accuracy of predicted patterns and/or physiological states with respect to the actual patterns and/or physiological states. Ground truth data may be used for comparing the detected patterns of motion (such as head bob, mirror checks, etc.) to the actual pattern of motion (at the present time) in order to verify and/or update the threshold values. The training model may be created and used using any now or hereafter known methods for using ground data for calibration purposes.

The system may then analyze 303 the patterns of motion detected over a period of time to determine a physiological state or physical action of the driver. As discussed above, examples of physiological states of a driver may include, without limitation, alert driver, focused driver, distracted driver, drowsy driver, fatigued driver, and other similar states. In an embodiment, a rule set may be defined for correlating the above detected patterns of motion to a physiological state of the driver. In an embodiment, various levels of the physiological states may also be defined. For example, more or less alert, highly distracted or less distracted, very focused, levels of fatigue or sleepiness, etc.

For example, a driver may be alert if he/she constantly checks the mirrors within the FMCSA suggested 5-8 second window. Other time interval windows are within the scope of this disclosure. Hence, an alert driver must check the mirrors at least once within the above time interval. A focused drivers may be determined if the driver spends over a threshold amount of the driving time looking at the road, and performing mirror checks. Distracted drivers are not focused. They often look out the windows or down. They check their mirrors less frequently, and are not looking at the road as often. If the driver is not looking at the mirrors or forward, then they are less focused or distracted. Alternatively and/or additionally, if the driver phone usage pattern of motion is detected, then the driver may be determined to be much less focused. In an embodiment, fatigued drivers may be determined by how often the driver is checking their mirrors compared to their typical behavior. Similarly, if rhythmic and/or swaying type of pattern of motion is detected, the driver is determined to be significantly fatigued. Additionally/and or optionally, a head bob may be indicative of a sleepy or very fatigued state of the driver.

In another embodiment, a score may be assigned to each of the above discussed detected patterns of motion to determine the physiological state of the driver. In an embodiment, positive events (i.e., corresponding to good driving behavior) may be given positive scores, and negative events (i.e., corresponding to bad driving behavior) may be given negative scores. For example, in an embodiment, a detected head bob may be assigned a score of −2, checking of mirrors every 5-8 seconds may be assigned a score of 3, a swaying pattern of motion may be assigned a score of −1, a hard brake may be assigned a score of −1, a phone usage pattern of motion may be assigned a score of −3, and so on. An overall score may be calculated at fixed time intervals and a driver physiological state may be determined based on the overall score. For example, a score of 10 or more may mean an alert driver, a score of 5-10 may mean a focused driver, a score of 0-5 may mean a distracted driver, a score of −5-0 may mean a fatigued driver, and a score of less than −5 may mean a sleepy driver. The above scores and score ranges are provided merely as example and other comparing mechanisms, scores, and score ranges are within the scope of this disclosure. The fixed time intervals may be pre-determined and/or calculated based on ground truth data as discussed above.

While the above discussion describes determining a physiological state of the driver at fixed time intervals, in an embodiment, the time interval may be adjusted dynamically based on the type of the pattern of motion detected in step 302. For example, if a threshold number of head-bob patterns of motion a detected, the time interval may be reduced. However, if the mirror checks are performed every 5-8 seconds for a threshold amount of time, the time interval may be increased.

In yet another embodiment, the above scoring may be continuously performed, and the physiological state may be determined and/or updated continuously based on the score.

In an embodiment, some of the detected patterns of motion may be not be used for determining the physiological state of the driver. For example, in an embodiment, a pattern of motion indicative of looking outside the window may be discounted if a lane change of the vehicle is observed following the outside looking pattern because a driver may need to check for blind spots before changing lanes. Similarly, a reduced frequency of mirror checks may be discounted in heavy traffic driving conditions. Alternatively and/or additionally, the above scoring may be adjusted to account for dangerous driving conditions such as increased negative scoring for failure to check mirrors before making a turn or before performing lane changes.

In this situation, the processor also may receive and use data received from an onboard diagnostics system (OBD) that monitors operational parameters of the vehicle. The processor may use the vehicle data to identify when the vehicle is turning. It may use the motion sensor data to identify that the driver failed to turn his/her head in a direction of the vehicle's turn, and thus could not have checked one or more mirrors, within a threshold period of time before the vehicle turning operation.

Next in step 304, the system may analyze whether the driver physiological state corresponds to a dangerous driving behavior and provide an alert 305 if dangerous driving behavior is recognized.

For example, in an embodiment, distracted, fatigued, and sleepy states determined, in step 303, for the driver may indicate dangerous driving behavior. The system could identify this as a dangerous situation and alert the driver accordingly and/or record this event. Or, it may alert a third party (such as a remote dispatcher) by generating an electronic communication that is transmitted to the third party. In addition, it may generate an alert that is recorded in a log file.

Alternatively and/or additionally, the system may also determine dangerous driving behavior based on the detected patterns of motion in step 302. Some detected patterns of motions may correspond to dangerous driving behavior such as head-bobs, continuously looking outside or downwards, phone usage while driving, and other similar patterns. For example, in an embodiment, the system may also determine dangerous driving behavior and generate an alert while the driver is driving the vehicle at speed on a road, the system may detect that the driver is not looking forward at the road and therefore not aware of the status of the road ahead. The system could identify this as a dangerous situation and alert the driver accordingly and/or record this event. Or, it may alert a third party (such as a remote dispatcher) by generating an electronic communication that is transmitted to the third party. In addition, it may generate an alert that is recorded in a log file.

In an embodiment, the system may determine an overall score for the operator of the vehicle over a time period of interest. The system may determine the overall score by assigning a score to each of the physiological states determined for the operator during the time period of interest and using the scores to determine the overall score. In an embodiment, the physiological states corresponding to dangerous driving behavior may be assigned a negative score or a low score compared to the scores assigned to physiological states corresponding to non-dangerous driving behavior. In an embodiment, the overall score may be indicative of a quality of the operator of the vehicle, such as good driver, safe driver, cautious driver, bad driver, etc.

Optionally, the wearable device or the portable electronic device may include a speaker that can receive the generated alert and output an audible signal that corresponds to the alert. In addition or alternatively, the wearable device or the portable electronic device may include a vibrator that is configured to receive the generated alert and output a haptic signal, such as a vibration of the device, in response to the alert.

As discussed above, the wearable electronic device and/or the portable electronic device may also include or be in short range or near field communication with a geographic positioning sensor such as those present in global positioning system (GPS)-enabled devices. As the system receives data from the wearable device, it may associate that data with position data before or when storing the data in an electronic record, when transmitting the data to a remote system, or when generating an alert.

Referring back to FIG. 1, the system also may include a system 121 that is remote from the wearable electronic device 121 and the portable electronic device 111. The remote system 121 is in electronic communication the portable electronic device and/or the wearable electronic device and may include features such as a receiver 122, processor 123, transmitter 124 and data storage facility 125. The data storage facility 125 may include profile data for multiple vehicle operators. When the remote system 121 receives pattern of motion data and/or driver physiological state data from an operator's electronic device, it may store that data in the data storage facility as part of a profile for the operator.

The remote system 121 and/or the portable device 111 may include instructions that cause the device's processor to also analyze the received pattern of motion data and/or driver physiological state data with previously-stored patterns for the driver to generate a score for the driver. For example, behaviors consistent with good or poor driving behaviors may be detected, such as frequently checking both side mirrors of the truck as a good behavior and spending an excessive amount of time looking at the radio or other item inside the truck as a poor behavior. A cumulative score (as discussed above) may be calculated that takes into account the good and poor behaviors, assigning good behaviors a positive score and poor behaviors a negative score. If any of the devices is also configured to receive monitored parameters from an OBD of the vehicle, then when generating the score for the operator, the applicable processor may also implement instructions to correlate one or more of the monitored parameters with the pattern of motion. Driving behaviors, such as hard braking, sharp steering and improper shifting of gears may be assigned a score that is included in the aggregate score for driver performance. The system or device may output the score via an electronic message, visual output, audio output, or as a printed document using a print device.

Figure 6:
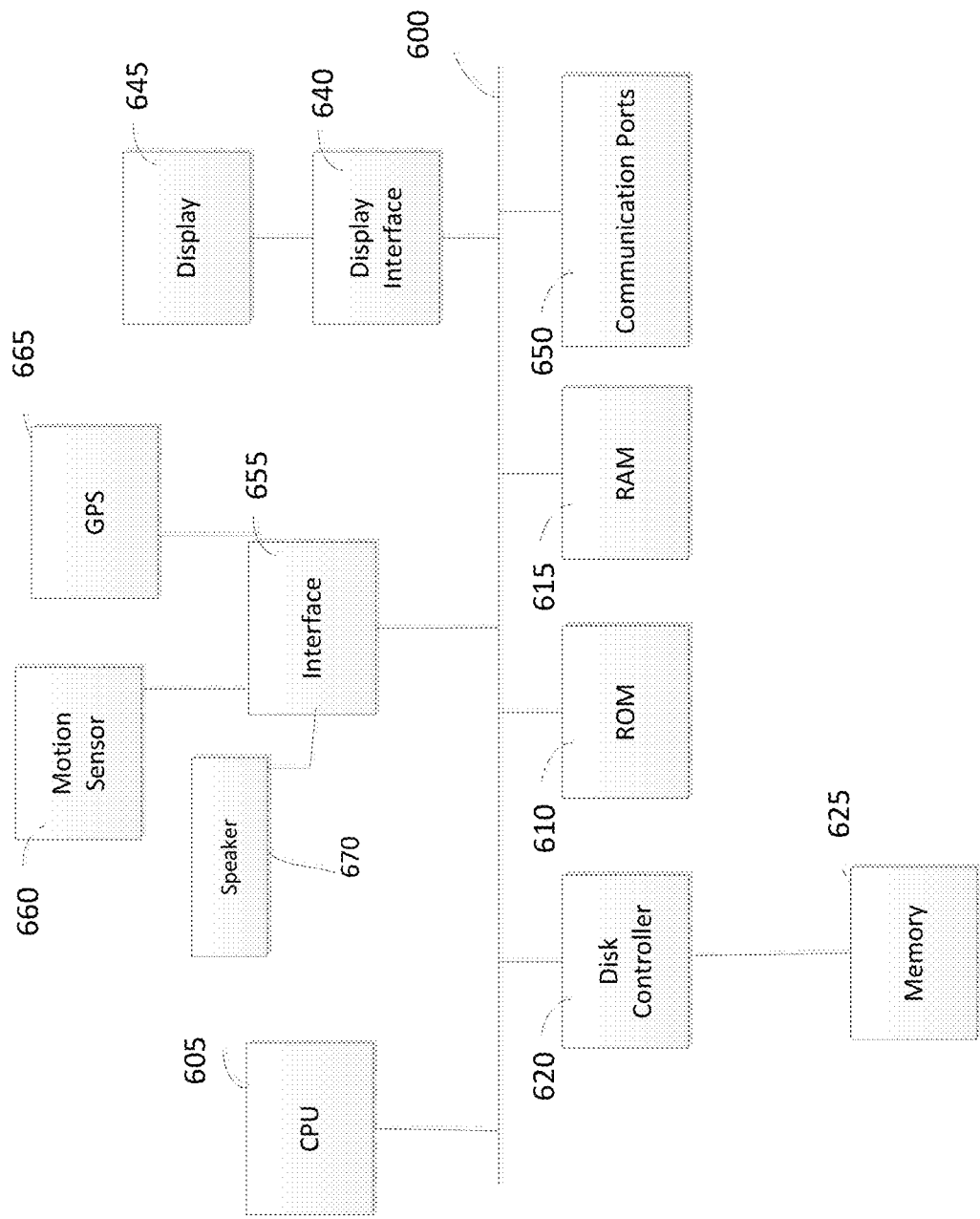
FIG. 6 illustrates example embodiments of an electronic device.

FIG. 6 depicts an example of internal hardware that may be used to contain or implement the various computer processes and systems as discussed above. For example, the wearable electronic device, the portable electronic device, and/or the remote system discussed above may include hardware such as that illustrated in FIG. 6. An electrical bus 600 serves as an information highway interconnecting the other illustrated components of the hardware. CPU 605 is a central processing unit of the system, performing calculations and logic operations required to execute a program. CPU 605, alone or in conjunction with one or more of the other elements, is a processing device, computing device or processor as such terms are used within this disclosure. A CPU or "processor" is a component of an electronic device that executes programming instructions. The term "processor" may refer to either a single processor or to multiple processors that together implement various steps of a process. Unless the context specifically states that a single processor is required or that multiple processors are required, the term "processor" includes both the singular and plural embodiments. Read only memory (ROM) 610 and random access memory (RAM) 615 constitute examples of memory devices. The term "memory device" and similar terms include single device embodiments, multiple devices that together store programming or data, or individual sectors of such devices.

A controller 620 interfaces with one or more optional memory devices 625 that service as data storage facilities to the system bus 600. These memory devices 625 may include, for example, an external or internal disk drive, a hard drive, flash memory, a USB drive or another type of device that serves as a data storage facility. As indicated previously, these various drives and controllers are optional devices. Additionally, the memory devices 625 may be configured to include individual files for storing any software modules or instructions, auxiliary data, incident data, or one or more databases for storing the information as discussed above.

Program instructions, software or interactive modules for performing any of the functional steps associated with the processes as described above may be stored in the ROM 610 and/or the RAM 615. Optionally, the program instructions may be stored on a non-transitory, computer readable medium such as a compact disk, a digital disk, flash memory, a memory card, a USB drive, an optical disc storage medium, and/or other recording medium.

An optional display interface 640 may permit information from the bus 600 to be displayed on the display 645 in audio, visual, graphic or alphanumeric format. Communication with external devices may occur using various communication ports 650. A communication port 650 may be attached to a communications network, such as the Internet, a local area network or a cellular telephone data network.

The hardware may also include an interface 655 which allows for receipt of data from input devices such as a motion sensor 660 or other input device 665 such as a GPS, a keyboard, a joystick, a touchscreen, a remote control, a pointing device, a video input device and/or an audio input device (such as a speaker 670).

The features and functions described above, as well as alternatives, may be combined into many other different systems or applications. Various alternatives, modifications, variations or improvements may be made by those skilled in the art, each of which is also intended to be encompassed by the disclosed embodiments.

The invention claimed is:

1. A system for monitoring behavior of an operator of a vehicle, comprising:
 a wearable electronic device configured to be worn on the head of an operator of the vehicle, wherein the wearable electronic device comprises a motion sensor; a processor; and
 a non-transitory computer-readable medium containing programming instructions that, when executed by the computer, cause the processor to:
 receive a first set of data from the motion sensor,
 analyze the first set of data to detect a pattern of motion that comprises a head rotational motion of the operator of the vehicle by:
 determining a forward-facing direction position as a position corresponding to the most common orientation of the wearable device,
 determining, based on the first set of data from the motion sensor, angular displacement of the operator's head, and
 determining whether the angular displacement corresponds to a phone usage event, wherein the phone usage event remained constant for at least a threshold period of time,
 access a data set corresponding to a plurality of patterns of motion,
 use the data set corresponding to the plurality of patterns of motion to analyze the detected pattern of motion and determine a physical behavior of the operator of the vehicle based on the detected pattern of motion by determining that the operator exhibited dangerous operator behavior if the system detected a phone usage event for at least a threshold period of time, and
 generate an alert if the determined physical behavior corresponds to a dangerous operator behavior.

2. The system of claim 1, further comprising a reference device that is attached to the vehicle and that includes:
 a transmitter, and
 a reference device motion sensor that is configured to collect a second set of data corresponding to motion of the vehicle.

3. The system of claim 2, wherein the instructions are further configured to cause the processor to:
 receive the second set of data from the transmitter; and
 determine that the physical behavior also corresponds to a hard braking event if:
 the first set of data indicates that the motion sensor of the wearable electronic device is experiencing a negative acceleration above a threshold value, and at the same time, the second set of data also indicates that the motion sensor of the reference device is experiencing a negative acceleration above a threshold value.

4. The system of claim 2, wherein the instructions are further configured to cause the processor to:
receive the second set of data from the transmitter; and
determine that the physical behavior also corresponds to a sudden lane change event if:
the first set of data indicates that the motion sensor of the wearable electronic device is experiencing a rate of change of direction in a z-plane relative to the earth exceeding a threshold value within a threshold time, and
at the same time, the second set of data also indicates that the motion sensor of the reference device is experiencing is experiencing a rate of change of direction in the z-plane relative to the earth exceeding the threshold value within the threshold time.

5. The system of claim 2, wherein the instructions are further configured to cause the processor to:
receive the second set of data from the transmitter,
analyze a derivative of the first set of data and the second set of data, and
determine that the physical behavior also corresponds to a hard steering event if the derivative has a value that exceeds a threshold.

6. The system of claim 1, wherein the wearable electronic device also comprises a housing, and the first processor and the non-transitory computer-readable medium are included within the housing.

7. The system of claim 1, further comprising a portable electronic device having a receiver, and wherein:
the wearable electronic device comprises a transmitter configured to transmit the first set of data to the receiver of the portable electronic device; and
the processor and the non-transitory computer-readable medium are included within the portable electronic device.

8. A method for monitoring behavior of an operator of a vehicle, comprising, by a processor:
receiving, from a motion sensor of a wearable electronic device, a first set of data associated with movement of the head of an operator of the vehicle wearing the wearable electronic device;
analyzing the first set of data to detect a pattern of motion that comprises a head rotational motion of the operator of the vehicle by:
determining a forward-facing direction position as a position corresponding to the most common orientation of the wearable device,
determining, based on the first set of data from the motion sensor, angular displacement of the operator's head, and
determining whether the angular displacement corresponds to a phone usage event, wherein the phone usage event remained constant for at least a threshold period of time;
accessing a data set corresponding to a plurality of patterns of motion;
using the data set corresponding to the plurality of patterns of motion to analyze the detected pattern of motion and determining that the operator exhibited dangerous operator behavior if the system detected a phone usage event for at least a threshold period of time; and
generating an alert if the system determined that the operator exhibited dangerous operator behavior.

9. The method of claim 8, further comprising collecting a second set of data corresponding to motion of the vehicle using a reference device motion sensor of a reference device that is attached to the vehicle.

10. The method of claim 9, further comprising:
receiving, at the processor, the second set of data from a transmitter of the reference device; and
determining that the physical behavior also corresponds to a hard braking event if:
the first set of data indicates that the motion sensor of the wearable electronic device is experiencing a negative acceleration above a threshold value, and
at the same time, the second set of data also indicates that the reference motion sensor is experiencing a negative acceleration above a threshold value.

11. The method of claim 9, further comprising:
receiving, at the processor, the second set of data from a transmitter of the reference device; and
determining that the physical behavior also corresponds to a sudden lane change event if:
the first set of data indicates that the motion sensor of the wearable electronic device is experiencing a rate of change of direction in a z-plane relative to the earth exceeding a threshold value within a threshold time, and
at the same time, the second set of data also indicates that the reference motion sensor is experiencing is experiencing a rate of change of direction in the z-plane relative to the earth exceeding the threshold value within the threshold time.

12. The method of claim 9, further comprising, by the processor:
receiving the second set of data from a transmitter of the reference device,
analyzing a derivative of the first set of data and the second set of data, and determining that the physical behavior also corresponds to a hard steering event if the derivative has a value that exceeds a threshold.

* * * * *